(12) United States Patent
Albert et al.

(10) Patent No.: US 10,478,793 B2
(45) Date of Patent: Nov. 19, 2019

(54) REACTOR FOR CARRYING OUT EQUILIBRIUM-LIMITED REACTIONS

(71) Applicant: Siemens Aktiengesellschaft, Munich (DE)

(72) Inventors: Jakob Albert, Rathsberg (DE); Manfred Baldauf, Erlangen (DE); Jenny Reichert, Schwanfeld (DE); Katharina Stark, Erlangen (DE); Alexander Tremel, Möhrendorf (DE); Peter Wasserscheid, Erlangen (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 0 days.

(21) Appl. No.: 16/086,726

(22) PCT Filed: Feb. 28, 2017

(86) PCT No.: PCT/EP2017/054602
§ 371 (c)(1),
(2) Date: Sep. 20, 2018

(87) PCT Pub. No.: WO2017/162410
PCT Pub. Date: Sep. 28, 2017

(65) Prior Publication Data
US 2019/0060859 A1    Feb. 28, 2019

(30) Foreign Application Priority Data
Mar. 22, 2016   (DE) .................. 10 2016 204 717

(51) Int. Cl.
*B01J 8/02*       (2006.01)
*B01J 8/10*       (2006.01)
*C07C 29/151*     (2006.01)

(52) U.S. Cl.
CPC ........... *B01J 8/0257* (2013.01); *B01J 8/0221* (2013.01); *B01J 8/10* (2013.01); *C07C 29/1518* (2013.01);
(Continued)

(58) Field of Classification Search
CPC ........ B01J 8/0285; B01J 8/0278; B01J 8/009; B01J 19/1881; B01J 19/1893;
(Continued)

(56) References Cited

U.S. PATENT DOCUMENTS

| 2,411,760 A | 11/1946 | Sensel ............................. 518/706 |
| 3,287,086 A | 11/1966 | Cahn ............................... 423/359 |

(Continued)

FOREIGN PATENT DOCUMENTS

| DE | 1301524 B      | 8/1969 | ................ B01F 5/10 |
| WO | 2017/162410 A1 | 9/1917 | ................ B01J 8/00  |

(Continued)

OTHER PUBLICATIONS

U.S. Non-Final Office Action, U.S. Appl. No. 16/086,763, 13 pages, dated Mar. 26, 2019.
(Continued)

*Primary Examiner* — Lessanework Seifu
(74) *Attorney, Agent, or Firm* — Slayden Grubert Beard PLLC

(57) ABSTRACT

Various embodiments may include a reactor for carrying out equilibrium-limited reactions comprising: a reaction chamber for receiving a catalyst; a sorption chamber for receiving a sorption agent; a feedstock feeding device; a sorption agent feeding device; and a gas-permeable element separating the reaction chamber from the sorption chamber, wherein the gas-permeable element repels particles of the sorption agent.

18 Claims, 2 Drawing Sheets

(52) U.S. Cl.
CPC .............. *B01J 2208/00814* (2013.01); *B01J 2208/00867* (2013.01); *B01J 2208/00884* (2013.01); *B01J 2208/00893* (2013.01); *B01J 2208/00911* (2013.01)

(58) Field of Classification Search
CPC ... B01J 2219/00076; B01J 2219/00168; C07C 29/152
See application file for complete search history.

(56) References Cited

U.S. PATENT DOCUMENTS

| | | | | |
|---|---|---|---|---|
| 3,310,367 | A | | 3/1967 | Mavrovic ..................... 423/420 |
| 3,471,424 | A | | 10/1967 | Tobin ............................ 523/309 |
| 4,731,387 | A | | 3/1988 | Westerterp .................... 518/706 |
| 4,790,915 | A | * | 12/1988 | Winsel ...................... C25B 1/46 205/515 |
| 4,968,722 | A | | 11/1990 | Westerterp .................... 518/706 |
| 5,712,313 | A | | 1/1998 | Kramer et al. ............... 518/706 |
| 7,279,145 | B2 | * | 10/2007 | Balan .................. B01D 29/018 422/239 |
| 7,470,825 | B2 | | 12/2008 | Lattner ......................... 568/909 |
| 2003/0086853 | A1 | | 5/2003 | Devic .......................... 423/272 |
| 2004/0033194 | A1 | * | 2/2004 | Amendola ............ B01J 23/462 48/61 |
| 2004/0048938 | A1 | | 3/2004 | Mohedas et al. ............. 518/726 |
| 2007/0021514 | A1 | | 1/2007 | Lattner ......................... 518/726 |
| 2007/0248849 | A1 | | 10/2007 | Preidel et al. ................ 429/437 |
| 2012/0027661 | A1 | | 2/2012 | Shiflett et al. ................ 423/359 |

FOREIGN PATENT DOCUMENTS

| | | | |
|---|---|---|---|
| WO | 2017/162513 A1 | 9/1917 | .............. B01J 19/18 |
| WO | 97/41953 A1 | 11/1997 | .............. B01J 10/00 |
| WO | 2009/106231 A1 | 9/2009 | ................ B01J 8/02 |
| WO | 2015/030578 A1 | 3/2015 | ........... C07C 29/152 |

OTHER PUBLICATIONS

International Search Report and Written Opinion, Application No. PCT/EP2017/054602, 8 pages, dated May 19, 2017.
International Search Report and Written Opinion, Application No. PCT/EP2017/056247, 10 pages, dated May 22, 2017.
European Office Action, Application No. 17709395.2, 6 pages, dated May 17, 2019.
U.S. Final Office Action, U.S. Appl. No. 16/086,763, 16 pages, dated Aug. 23, 2019.
Australian Office Action, Application No. 2017238995, 4 pages, dated Aug. 1, 2019.

* cited by examiner

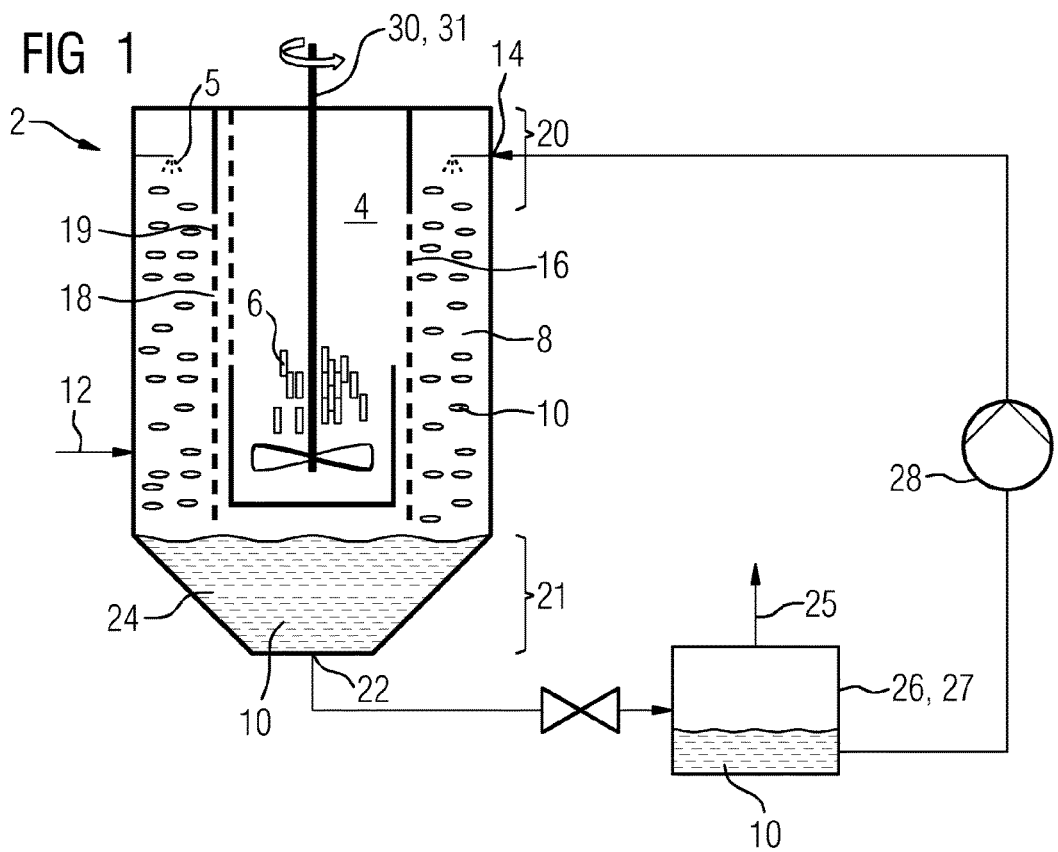
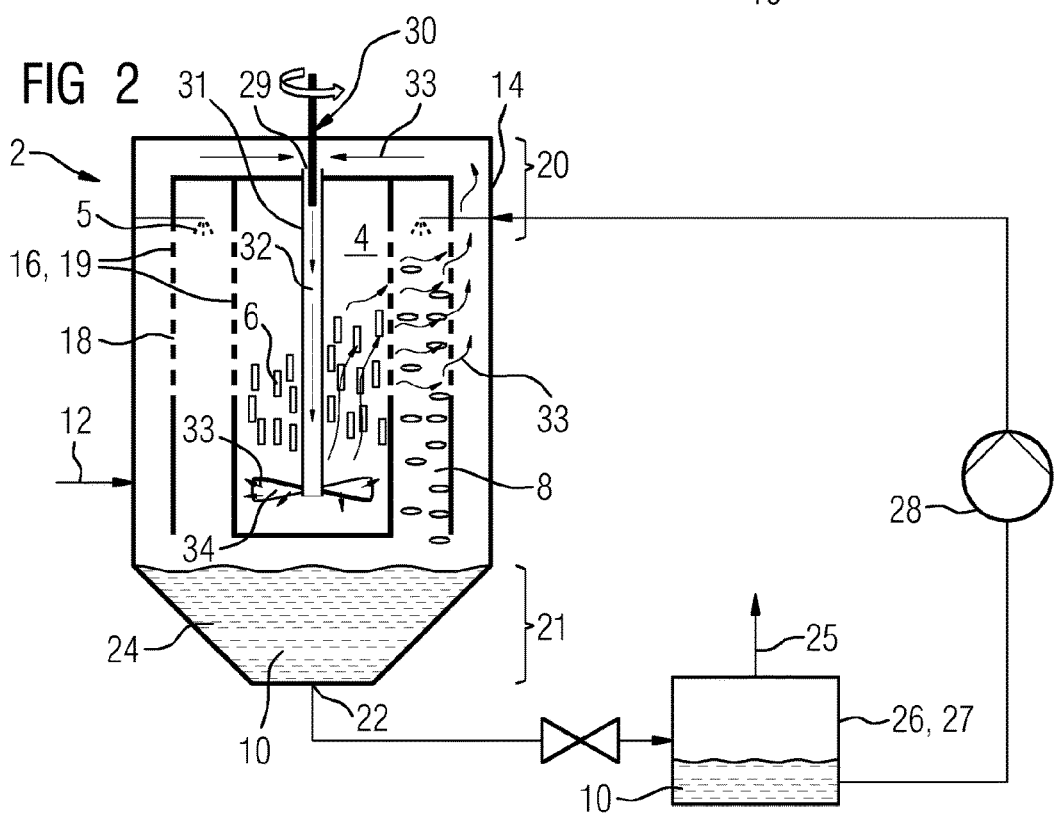

REACTOR FOR CARRYING OUT EQUILIBRIUM-LIMITED REACTIONS

CROSS-REFERENCE TO RELATED APPLICATIONS

This application is a U.S. National Stage Application of International Application No. PCT/EP2017/054602 filed Feb. 28, 2017, which designates the United States of America, and claims priority to DE Application No. 10 2016 204 717.5 filed Mar. 22, 2016, the contents of which are hereby incorporated by reference in their entirety.

TECHNICAL FIELD

The present disclosure relates to reactors. Various embodiments may include a reactor for carrying out equilibrium-limited reactions.

BACKGROUND

Very many chemical reactions, which are of industrial significance, are equilibrium-limited. This means that the reaction between the reaction starting materials to the reaction products does not proceed completely on adjustment of a chemical equilibrium and does not lie completely on the product side. In the chemical equilibrium, therefore, products and starting materials are always present alongside one another. In the case of conventional chemical syntheses, these are, for example, the reactions for the production of methanol from hydrogen and carbon monoxide or carbon dioxide or the production of ammonia from hydrogen and nitrogen, the so-called Haber-Bosch process.

These reactions are carried out industrially nowadays in heterogeneously catalyzed fixed bed or slurry reactors. As described, the starting materials are only partially converted in a single pass through the reactor. Subsequently, the reactant-product mixture is withdrawn and the reaction products are typically separated, wherein the unreacted starting materials are recirculated to a reaction inlet point. The recirculation of partly large amounts of gases on an industrial scale results in high apparatus complexity. Furthermore, still further technical challenges arise, which in their entirety have a distinctly cost-intensive impact on the process.

In practice, there is a loss of pressure in the reactor which has to be compensated for in the case of a significant recirculation. Furthermore, in the case of recirculation, inert and foreign gases accumulate in the circuit, which has a negative influence on the reaction regime and results in a larger reactor volume for example. Furthermore, in the case of recirculation, there is always a loss of starting material which in turn has a negative effect on the conversion efficiency. Furthermore, the amount of gas recycled leads to a high gas volume flow through the reactor which increases the size and thus in turn the costs of the reactor.

SUMMARY

The teachings of the present disclosure may be embodied in a reactor for carrying out equilibrium-limited reactions which have a smaller size compared to the prior art and can be operated more economically. For example, some embodiments include a reactor for carrying out equilibrium-limited reactions, comprising a reaction chamber (4) for receiving a catalyst (6) and further comprising a sorption chamber suitable for receiving a sorption agent (10), and also a feedstock feeding device (12) and a sorption agent feeding device (14), characterized in that the reaction chamber (4) and the sorption chamber are separated by a gas-permeable element (16) that repels liquid drops or particles of the sorption agent (10).

In some embodiments, the element (16) has passage openings (18) having a diameter of less than 100 μm, preferably less than 10 μm, particularly preferably less than 5 μm.

In some embodiments, the element (16) is configured in the form of a textile. In some embodiments, the textile comprises metallic fibers.

In some embodiments, the element (16) is configured in the form of a metal mesh (19), metal gauze or an expanded metal.

In some embodiments, the element (16) comprises a membrane.

In some embodiments, the sorption agent feeding device (14) is provided in an upper region (20) of the reactor (4) and that a sorption agent discharge device (22) is provided in a lower region.

In some embodiments, a liquid drop repellent effect of the element (16) decreases from the upper region (20) to the lower region (21).

In some embodiments, a sorption agent collection zone (24) is arranged in the lower region (21) of the reactor (2).

In some embodiments, a product separation device (26) is provided which is provided externally to the reaction chamber (4) and externally to the sorption chamber (8).

In some embodiments, the product separation device (26) is configured in the form of a phase separator (27) for the separation of reaction products and sorption agent (10).

In some embodiments, a sorption agent conveying device (28) is provided between the product separation device (26) and the sorption agent feeding device (14).

In some embodiments, a suction device (29) is provided in the upper region for circulating a gas phase from the sorption chamber (8) into the reaction chamber (4).

In some embodiments, the suction device (29) is at least partially integrated in a stirring device (30) and a stirring shaft (31) forms a flow channel (32) of the suction device (29).

As another example, some embodiments include a method for operating an equilibrium-limited reaction, wherein gaseous reaction starting materials (5) and a liquid sorption agent (10) are introduced into a sorption chamber (8) of a reactor (2), wherein a reaction chamber (4) is further provided in which a catalyst (6) is arranged and the gaseous reaction products (5) flow through an element (16) by means of which the reaction chamber (4) is separated from the sorption chamber (8), wherein at the same time the penetration of the liquid sorption agent (10) into the reaction chamber (8) is prevented by means of the element (16).

BRIEF DESCRIPTION OF THE DRAWINGS

Further configurations and/or embodiments of the teachings herein and further features are elucidated in more detail with the aid of the following figures. These show:

FIG. 1 a reactor having a sorption chamber and a reaction chamber, which are separated by an appropriate element, according to teachings of the present disclosure;

FIG. 2 a reactor in accordance with FIG. 1 with an additional circulation of the gas phase in the reaction chamber and the sorption chamber;

DETAILED DESCRIPTION

Figure 3:
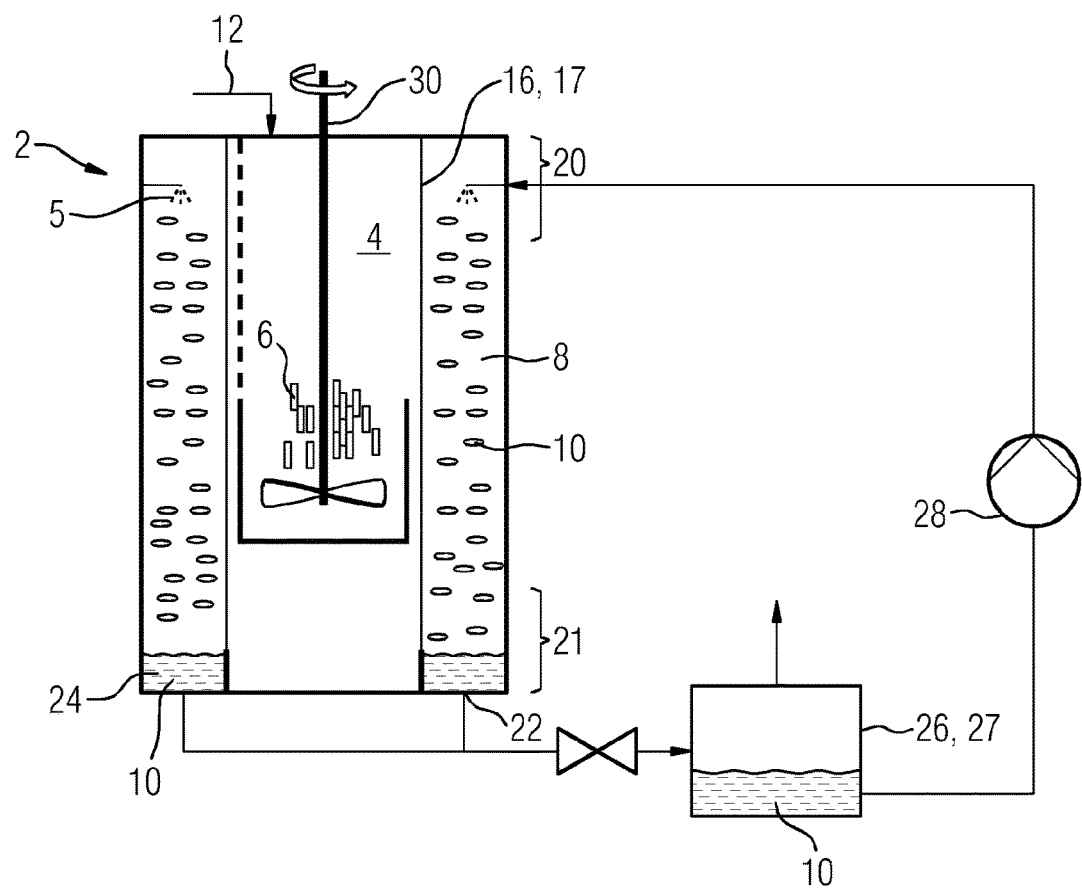
FIG. 3 a reactor in accordance with FIG. 1, in which the separating element between the sorption chamber and reaction chamber is configured by means of a membrane.

In some embodiments, a reactor for carrying out equilibrium-limited reactions comprises a reaction chamber for receiving a catalyst and further a sorption chamber suitable for receiving a sorption agent. In addition, the reactor comprises a feedstock feeding device and a sorption agent feeding device. The reactor is characterized in that the reaction chamber and the sorption chamber are separated by a gas-permeable element that repels liquid drops or particles of the sorption agent. Liquid sorption agents are generally used, although in principle solids may also serve as sorption agent which are fine-grained in particle form. The separation of reaction chamber and sorption chamber is achieved by an appropriate element that allows gaseous starting materials and products to flow unhindered back and forth between the reaction chamber and the sorption chamber, while the liquid drops of the sorption agent remain in the sorption chamber and cannot get into the reaction chamber. Separation of these liquid drops from the reaction chamber is thus appropriate, since in the case of contact of the catalyst material with the liquid sorption agent, the mode of action of the reactor material is impaired.

In some embodiments, passage openings of the element have a diameter of less than 100 μm, less than 10 μm, or less than 0.5 μm. Depending on the viscosity of the sorption agent, which is often in the form of an aqueous solution, an oil or ionic liquids, and depending on the wetting of the element surface by the sorption agent, the width or the diameter of the passage opening can or must be adjusted accordingly.

In some embodiments, the element is configured in the form of a textile, especially with fibers, which are based on glass, metallic materials, ceramic materials or carbon. In this case, the use of a metal mesh, the use of a metal gauze or an expanded metal is especially effective. In some embodiments, the element is configured in the form of a membrane which is characterized by selective permeability to the starting materials and products and is in this case liquid-repellent.

In some embodiments, the reactor has an upper region and a lower region, in which a sorption agent feeding device is provided in the upper region and a sorption agent discharge device is provided in the lower region. Therefore, sorption agent laden with products can be removed from the reactor and unladen sorption agent can be fed back again by means of the feeding device.

In some embodiments, the effect of the element to repel liquid drops is variable and therefore decreases from the upper region to the lower region of the reactor. In some embodiments, the sorption agent feeding device is provided in the upper region and liquid sorption agent is introduced and sprayed into this region. In some embodiments, a greater repellent effect to liquid drops through the element exists in this region. Therefore, for example, when using a textile element, the diameter of the passage openings or the mesh size can be increased from the upper region to the lower region. This can also mean that, by implication, the permeability to liquid drops through the element in the upper region is completely suppressed or this region is completely sealed.

In some embodiments, a sorption agent collection zone is arranged in the lower region of the reactor in which laden sorption agent is concentrated. From there, it is convenient in turn to remove the laden sorption agent from the reactor and to feed it to a product separation device which is arranged externally to the reaction chamber and externally to the sorption chamber. This product separation device is part of the reactor, but located externally to the reaction chamber and sorption chamber, which together form a reactor core. The product separation device is suitable for separating the sorption agent from the product and to discharge the product from the reaction process.

The sorption agent thus separated from the product can be fed, e.g. by means of a sorption agent conveying device, from the product separation device to the sorption agent feeding device of the reactor. This means in turn that the sorption agent which has been withdrawn from the reactor is recirculated and is fed again as fresh sorption agent to the reactor.

In some embodiments, a suction device is provided in the upper region of the reactor for circulating a gas phase from the sorption chamber into the reaction chamber. By these means, a better exchange of the gaseous starting materials and products through the two chambers, the reaction chamber and the sorption chamber, is enabled and the supply of starting materials to the catalyst surface is enhanced. Also, the products are discharged from the catalyst to a greater degree and fed to the sorption agent in the sorption chamber. In some embodiments, this suction device is integrated at least partially in a stirring device and a stirring shaft forms a flow channel of the suction device. This has the advantage that the stirrer or the stirrer shaft and the stirrer blades are employed as part of the suction device for circulating the gas phase and fewer components have to be incorporated in the reaction chamber.

In some embodiments, gaseous reaction starting materials and a liquid sorption agent are introduced into a sorption chamber of a reactor. A reaction chamber is further provided in which a catalyst is arranged. The reaction chamber and the sorption chamber are separated by an element through which the gaseous reaction products flow from the reaction chamber to the sorption chamber. On the other hand, the reaction chamber is separated from the sorption chamber by the element such that at the same time penetration of the liquid sorption agent into the reaction chamber is prevented.

In some embodiments, it is possible to withdraw the reaction products from the catalyst surface and to add them to the sorption agent through which the products are discharged. At the same time, it is prevented that the sorption agent gets into the reaction chamber through the element and that therefore the mode of action of the catalyst is negatively affected.

In FIG. 1 a reactor 2 is depicted which serves for the reaction of equilibrium-limited reactions. The equilibrium position in this example reaction, under customary reaction conditions, e.g. 250° C. and 75 bar, is to an extent of 75% on the side of the starting materials carbon dioxide and hydrogen. The conversion to methanol (reaction product 25) takes place under these reaction conditions in an equilibrium position to an extent of only 25%.

In the reactor 2 depicted, with the aid of a feedstock feeding device 12, starting materials, e.g. gaseous starting materials, for example the carbon dioxide and hydrogen already mentioned, are fed to the reactor. In this case, the feeding is carried out into the sorption chamber 8, feeding into the reaction chamber 4, such as shown in FIG. 3 for example, is also suitable for all figures and working examples shown. The sorption chamber 8 is separated from a reaction chamber 4 by an element 16, 18. The element 16 is configured in a form that is impermeable to drops of a sorption agent 10.

In this case, the material of the element 16 is for example a textile, particularly a textile with a metal mesh, such as wire mesh, gauze, or an expanded metal. Other fiber fabrics, such as aramid fiber for example, or other high temperature-resistant fibers would also be appropriate as basic component of element 16. The element 16 has passage openings or open pores or meshes which are gas-permeable in their own right but which hold back the liquid drops of the sorption agent 10. A typical mesh size or passage opening width in this case is less than 100 μm, depending on the characteristics of the sorption agent 10. In some embodiments, the passage opening width may be less than 10 μm or less than 5 μm. The characteristics of the sorption agent 10 is understood to mean in particular its wetting angle compared to the element material and its viscosity.

A catalyst 6 is arranged in the reaction chamber 4, while in addition optionally a stirring device 30 is located in the reaction chamber 4. The catalyst may, for example, be hung in baskets or be present as gas-permeable bulk material. The catalyst material is selected so that it accelerates the reaction, in this case the reaction between carbon dioxide and hydrogen, in which it has a particularly large surface area. The equilibrium state itself cannot be influenced by the catalyst material.

In some embodiments, by means of a particular flow, which is discussed further hereinafter, or by stirring motion or by a combination of these measures, gaseous reaction products 25 are moved away from the catalyst surface and reach the sorption chamber 8 from the reaction chamber 4 through the element 16. There, the products are absorbed by droplets of the sorption agent 10. The droplets of the sorption material 10 thus laden sink down in the sorption chamber 8 and are collected in a lower region 21 of the reactor 2 in a sorption agent collection zone 24. The sorption agent 10 collected in this way is withdrawn from the sorption agent collection zone 24 and fed to a product separation device 26. The product separation device 26 is configured in the form of a phase separator 27, in which the reaction product 25 is separated from sorption agent 10 and is discharged.

The sorption agent 10, from which the reaction product 25 has been desorbed, is led away from the phase separator 27 by means of a sorption agent conveying device 28 and is conveyed to a sorption agent feeding device 14 in an upper region 20 of the reactor 2. The sorption agent feeding device 14 serves to introduce the sorption agent 10 into the reactor 2, more specifically into the sorption chamber 8. This is effected, for example, by a spray nebulizer. In this manner, the smallest possible sorption agent droplets are generated which can absorb the reaction products 25 particularly well due to an advantageous volume surface area ratio. The sorption agents can be present in the form of an aqueous solution, an oil or ionic liquids.

FIG. 2 gives an analogous depiction of a reactor 2 to that of FIG. 1, but in this case the gas feed to the reaction products 25 and starting materials is described more precisely. The arrows 33, which depict the overall gas flow in the reactor 2, represent the motion of the starting materials and the reaction products 25. Here, a suction device 29 is provided, which is part of a stirring device 30. The stirring device 30 has in turn a hollow stirring shaft 31 which serves as a flow channel 32 for the gas stream 33. Starting materials are aspirated in gaseous form by the suction device 29, sucked into the flow channel 32 and passed again into the reaction chamber by the stirrer blades 34 of the stirring device 30.

At this point, the starting materials are near to the catalyst 6 and can react on the surface thereof according to the reaction described to afford the reaction products 25. Reaction products 25 and the reaction starting materials described are passed again as a gas mixture with varying compositions along the reaction stream 33 through the element 16, which is also configured here in the form of a metal mesh 19, through the passage openings 18 of this metal mesh 19, into the sorption chamber 8. There, the reaction products 25, as a component of the gas stream 33, encounter the droplets of the sorption agent 10 and are absorbed by these. The starting materials which are not absorbed by the sorption agent are in turn aspirated by the suction device 29 along the arrows 33 depicted and again, as described, passed via the stirring device 30 into the sorption chamber 4.

FIG. 3 shows an analogous reactor 2 as in FIG. 1, but differs from the reactor in FIG. 1 in that, instead of a textile element 16, a membrane 17 ensures the separation between reaction chamber 4 and sorption chamber 8. In some embodiments, this membrane has a high selectivity for and a high permeability to the reaction products 25. In this manner, products are withdrawn from the equilibrium without removing starting materials from the reaction chamber. Depending on the selectivity and permeability, starting materials and reaction products may also of course diffuse together through the membrane, in which case it is appropriate, in analogy to FIG. 2, to install a suction device 29 which ensures a gas stream 33 in analogy with FIG. 2.

For example, if one of the starting materials is hydrogen, the danger exists that the hydrogen diffuses more rapidly through the membrane than the reaction products 25. In this case, the products 25 are separated from the hydrogen by dissolving in the sorption liquid 10 in the sorption chamber 8. This has in this case a lower solubility in the sorption agent 10. In this manner, the partial pressure of hydrogen in the sorption chamber 8 is increased, such that an equilibrium between the hydrogen content in the reaction chamber 4 and in the sorption chamber 8 is established, whereby the diffusion of hydrogen from the reaction chamber into the sorption chamber reaches a standstill.

What is claimed is:

1. A reactor for carrying out equilibrium-limited reactions, the reactor comprising:
   a reaction chamber for receiving a catalyst;
   a sorption chamber for receiving a sorption agent;
   a feedstock feeding device;
   a sorption agent feeding device;
   a sorption agent discharge device for removing sorption agent from a lower region of the reactor; and
   a gas-permeable element separating the reaction chamber from the sorption chamber, wherein the gas-permeable element repels particles of the sorption agent;
   wherein the sorption agent feeding device provides sorption agent to an upper region of the reactor; and
   the gas-permeable element exhibits a liquid drop repellent effect decreasing from the upper region to the lower region.

2. The reactor as claimed in claim 1, wherein the gas-permeable element comprises passage openings with a diameter of less than 100 μm.

3. The reactor as claimed in claim 1, wherein the gas-permeable element comprises a textile.

4. The reactor as claimed in claim 3, wherein the textile comprises metallic fibers.

5. The reactor as claimed in claim 1, wherein the gas-permeable element comprises a metal mesh, a metal gauze, or an expanded metal.

6. The reactor as claimed in claim 1, wherein the gas-permeable element comprises a membrane.

7. The reactor as claimed in claim 1, wherein a sorption agent collection zone collects the sorption agent in the lower region.

8. The reactor as claimed in claim 1, further comprising a product separation device external to the reaction chamber and to the sorption chamber.

9. The reactor as claimed in claim 8, wherein the product separation device comprises a phase separator for separation of reaction products and the sorption agent.

10. The reactor as claimed in claim 8, further comprising a sorption agent conveying device between the product separation device and the sorption agent feeding device.

11. The reactor as claimed in claim 1, further comprising a suction device in the upper region for circulating a gas phase from the sorption chamber into the reaction chamber.

12. The reactor as claimed in claim 11, wherein:
the suction device is at least partially integrated in a stirring device; and
a stirring shaft forms a flow channel of the suction device.

13. A method for operating an equilibrium-limited reaction, the method comprising:
introducing gaseous reaction starting materials and a liquid sorption agent into a sorption chamber of a reactor;
wherein the reactor comprises a reaction chamber with a catalyst therein;
wherein the reaction chamber and the sorption chamber are separated by a gas-permeable element allowing gaseous reaction products of the reaction to flow through the gas-permeable element;
preventing penetration of the liquid sorption agent into the reaction chamber with the gas-permeable element and repelling particles of the liquid sorption agent with the gas-permeable element;
removing sorption agent from a lower region of the reactor with a sorption agent discharge device; and
circulating a gas phase from the sorption chamber into the reaction chamber.

14. A reactor for carrying out equilibrium-limited reactions, the reactor comprising:
a reaction chamber for receiving a catalyst;
a sorption chamber for receiving a sorption agent;
a feedstock feeding device;
a sorption agent feeding device for providing sorption agent to an upper region of the reactor;
a sorption agent discharge device for removing sorption agent from a lower region of the reactor;
a suction device in the upper region of the reactor for circulating a gas phase from the sorption chamber into the reaction chamber; and
a gas-permeable element separating the reaction chamber from the sorption chamber, wherein the gas-permeable element repels particles of the sorption agent.

15. The reactor as claimed in claim 14, wherein the gas-permeable element comprises a textile.

16. The reactor as claimed in claim 14, wherein the gas-permeable element comprises a textile having metallic fibers.

17. The reactor as claimed in claim 14, wherein the gas-permeable element comprises a metal mesh, a metal gauze, or an expanded metal.

18. The reactor as claimed in claim 14, wherein:
the suction device is at least partially integrated in a stirring device; and
a stirring shaft forms a flow channel of the suction device.

* * * * *